United States Patent [19]

Townsend et al.

[11] Patent Number: 4,927,830

[45] Date of Patent: May 22, 1990

[54] ACYCLIC PYRROLO[2,3-D]PYRIMIDINE ANALOGS AS ANTIVIRAL AGENTS

[75] Inventors: Leroy B. Townsend; John C. Drach, both of Ann Arbor, Mich.

[73] Assignee: The Regents of the University of Michigan, Ann Arbor, Mich.

[21] Appl. No.: 179,081

[22] Filed: Apr. 8, 1988

[51] Int. Cl.$^5$ .................... C07D 401/04; A61K 31/40
[52] U.S. Cl. .................................... 514/258; 544/280; 544/243
[58] Field of Search ................. 544/280, 243; 514/258

[56] References Cited

U.S. PATENT DOCUMENTS 3,817,982  6/1974  Verheyden et al.
3,962,211  6/1976  Townsend et al.
4,229,453 10/1980  Roth et al.
4,596,798  6/1986  Shipman, Jr. et al.

FOREIGN PATENT DOCUMENTS 3036390  5/1982  Fed. Rep. of Germany ...... 544/280

OTHER PUBLICATIONS

Bergstom, D. et al., "Antiviral Activity of C-5 Substituted Tubercidin Analogues", *J. Med. Chem.*, 27:285-292 (1984).

Turk, S. R. et al., "Pyrrolo[2,3-d]Pyrimidine Nucleosides as Inhibitors of Human Cytomegalovirus", *Antimicrob. Agents Chemother.*, 31:544-550 (1987).

DeClercq, E. et al., "Antirhinovirus Activity of Purine Nucleoside Analogs", *Antimicrob. Agents Chemother.*, 29:482-484 (1986).

Shipman, C., Jr., "Antiviral Activity of Arabinosyladenine and Arabinosylhypoxanthine in Herpes Simplex Virus-Infected KB Cells: Selective Inhibition of Viral Deoxyribonucleic Acid Synthesis in Synchronized Suspension Cultures", *Antimicrob. Agents Chemother.*, 9:120-127 (1976).

Mitsuya, H. et al., "3-Azido-3'deoxythymidine (BW A509U): An Antiviral Agent that Inhibits the Infectivity and Cytopathic Effect of Human T-Lymphotropic Virus Type III/Lymphadenopathy-Associated Virus in vitro", *PNAS (U.S.A.)*, 82:7096-7100 (1985).

Mitsuya, H. et al., "Inhibition of the In Vitro Infectivity and Cytopathic Effect of Human T-Lymphotrophic Virus Type III/Lymphadenopathy-Associated Virus (HTLV-III/LAV) by 2',3'-Dideoxynucleosides", *PNAS (U.S.A.)*, 83:1911-1915 (1986).

Smith, C. M. et al., "Inhibitors of Hypoxanthine Metabolism in Ehrlich Ascites Tumor Cells in Vitro", *Cancer Treatment Reports*, 60:1567-1584 (1976).

Maruyama, T. et al., "Pyrrolopyrimidine Nucleosides, 18, Synthesis and chemotherapeutic Activity of 4-Amino-7-(3-Deoxy-$\beta$-D-Ribofuranosyl)Pyrrolo-[2,3-d]Pyrimidine-5-Carboxamide (3'-Deoxysangivamycin) and 4-Amino-7-(2-Deoxy-$\beta$-D-Ribofuranosyl)Pyrrolo[2,3-d]-Pyrimidine-5-Carboxamide (2'-Deoxysangivamycin)", *J. Med. Chem.*, 26:25-29 (1983).

DeClercq, E. et al., "Nucleic Acid Related Compounds, 51, Synthesis and Biological Properties of Sugar-Modified Analogues of the Nucleoside Antibodies Tubercidin, Toyocamycin, Sangivamycin, and Formycin", *J. Med. Chem.*, 30:481-486 (1987).

Hasske, F. et al., "2' and 3'-Ketonucleosides and their *Arabino* and *Xylo* Reduction Products", Tetrahedron 40:125-135 (1984).

Robins, M. J. et al., "A Mild Conversion of Vicinal Diols to Alkenes, Efficient Transformation of Ribonucleosides into 2'-ene and 2',3'-Dideoxynucleosides", *Tetrahedron Letters*, 25:367-370 (1984).

(List continued on next page.)

*Primary Examiner*—Mukund J. Shah
*Assistant Examiner*—C. L. Cseh
*Attorney, Agent, or Firm*—Harness, Dickey & Pierce

[57] ABSTRACT

This invention relates to the use of acyclic substituted pyrrolo[2,3-d]pyrimidine nucleoside analogs in the treatment of viral infections. Such substituted compounds retain antiviral properties present in their parent compounds, yet exhibit significantly decreased levels of cytotoxicity, thereby having therapeutic potential as antiviral agents.

26 Claims, 2 Drawing Sheets

OTHER PUBLICATIONS

Jain, T. C. et al., "Reactions of 2-Acyloxyisobutyryl Halides with Nucleosides, III, Reactions of Tubercidin and Formycin", *J. Org. Chem.* 38:3179–3186 (1973).

Tolman, R. L. et al., "Pyrrolopyrimidine Nucleosides, III, The Total Synthesis of Toyocamycin, Sangivamycin, Tubercidin, and Related Derivatives", *J. Am. Chem. Soc.*, 91:2102–2108 (1969).

Ramasamy, K. et al., "Total Synthesis of 2'-Deoxytoyocamycin, 2'-Deoxysangivamycin and Related 7-β-D-Arabinofuranosyl-Pyrrolo[2,3-d]Pyrimidines via Ring Closure of Pyrrole Precursors Prepared by the Sterospecific Sodium Salt Glycosylation Procedure", Nucleic Acid Research Institute, (Abstract 65).

Vindelov, L. L., "Flow Mirofluorometric Analysis of Nuclear DNA in Cells from Solid Tumors and Cell Suspensions", *Virchow's Arch. Cell Pathol.*, 24:227–242 (1977).

Gadler, H., "Nucleic Acid Hybridization for Measurement of Effects of Antiviral Compounds on Human Cytomegalovirus DNA Replication", *Antimicrob. Agents Chemother.*, 24:370–374 (1983).

Drach, J. C. et al., "Tritiated Thymidine Incorporation Does Not Measure DNA Synthesis in Ribavirin--Treated Human Cells", *Science*, 212:549–551 (1981).

Shipman, C. Jr., et al., "Evaluation of 4-(2-Hydroxyethyl)-1-piperazineethane-Sulfonic Acid (HEPES) as a Tissue Culture Buffer", *Proc. Soc. Exp. Biol. Med.* 120:305–310 (1969).

FIG. 1.

ACYCLIC PYRROLO[2,3-D]PYRIMIDINE ANALOGS AS ANTIVIRAL AGENTS

This invention was made with Government support under contracts numbered NO1AI42554 and NO-1AI72641 awarded by the National Institute of Allergy and Infectious Diseases. The Government has certain rights in this invention.

BACKGROUND OF THE INVENTION

The present invention relates to the use of certain deazapurine nucleoside analogs in the treatment of viral infections. More particularly, the present invention relates to the use of certain pyrrolo[2,3-d]pyrimidine nucleoside analogs against human cytomegalovirus and herpes simplex virus type 1.

Broad spectrum antiviral activity of pyrrolo[2,3-d]pyrimidine nucleosides such as tubercidin, sangivamycin and toyocamycin and some substituted derivatives has been previously reported. Activity of those compounds against specific viruses, such as RNA rhinovirus and DNA herpes simplex virus type 1 and type 2 has also been reported. See, for example, Bergstron D. E., Brattesani A. J., Ogawa M. K., Reddy P. A., Schweickert M. J., Balzarini J., Declercq E., *J. Med. Chem.*, 27, 285–292, (1984) and DeClercq E., Bernaerts R., Bergstrom D. E., Robins M. J., Montgomery J. A., Holy A., *Antimicrob. Agents Chemother.*, 29, 482–284, (1986).

Pyrrolo[2,3-d]pyrimidine nucleosides are particularly attractive as potential antiviral agents because of their stability toward the two major pathways of bioactive purine nucleoside inactivation, deamination by adenosine deaminase and glycosidic bond cleavage by purine nucleoside phosphorylases. Unfortunately, pyrrolo[2,3-d]pyrimidine nucleosides which have been previously described as potently antiviral also exhibit unacceptable levels of cytotoxicity, thereby diminishing their usefulness in the treatment of viral infections in animals.

It would thus be very desirable to discover derivatives of these compounds having decreased cytotoxicity while retaining their antiviral properties. Such a discovery has been made and is the basis for the present invention which relates to a class of 4, 5, 6, 7-substituted pyrrolo[2,3-d]pyrimidine analogs which exhibit levels of cytotoxicity significantly lower than their parent compounds, yet retain antiviral activity, particularly against DNA human cytomegalovirus (HCMV) and herpes simplex virus type 1 (HSV-1).

SUMMARY OF THE INVENTION

The present invention relates to the treatment of viral infections, and, more particularly, human cytomegalovirus (HCMV) and herpes simplex virus type 1 (HSV-1) infections, with a therapeutically-effective amount of a compound selected from a group consisting of compounds of the following formula and pharmaceutically acceptable salts thereof:

where
$R_1$ is $NH_2$ or NHOH;
$R_2$ is $CSNH_2$, Cl, Br, I, F, 2-buten-1-yl, 5-(1-hydroxyethyl) or 5-(1-methoxyethyl);
$R_3$ is H, $NH_2$ or Br; and
$R_4$ is (1,3-dihydroxy-2-propoxy)methyl, (2-hydroxyethoxy)methyl, (2-ethoxy)methyl, (2-acetoxyethoxy)methyl, 2-hydroxy-1-(1,3-dihydroxy-2-propoxy)ethyl, (2-phosphonylmethoxy)ethyl or 3-hydroxy-2-phosphonylmethoxypropyl.

DESCRIPTION OF THE INVENTION

A. Chemical Structure of Compounds

The present invention relates to the treatment of viral infections with pyrrolo[2,3-d]pyrimidine analogs of the following formula and pharmaceutically acceptable salts thereof:

where
$R_1$ is $NH_2$ or NHOH;
$R_2$ is $CSNH_2$, Cl, Br, I, F, 2-buten-1-yl, 5-(1-hydroxyethyl) or 5-(1-methoxyethyl);
$R_3$ is H, $NH_2$ or Br; and
$R_4$ is (1,3-dihydroxy-2-propoxy)methyl, (2-hydroxyethoxy)methyl, (2-ethoxy)methyl, (2-acetoxyethoxy)methyl, 2-hydroxy-1-(1,3-dihydroxy-2-propoxy)ethyl, (2-phosphonylmethoxy)ethyl or 3-hydroxy-2-phosphonylmethoxypropyl.

Preferred specific compounds include the following:

1. 4-amino-5-chloro-7-(2-hydroxyethoxymethyl)pyrrolo [2,3-d]pyrimidine, where $R_1$ is $NH_2$, $R_2$ is Cl, $R_3$ is H and $R_4$ is —$CH_2$—$OCH_2$—$CH_2OH$;
2. 4-amino-5-bromo-7-(2-hydroxyethoxymethyl)pyrrolo [2,3-d]pyrimidine, where $R_1$ is $NH_2$, $R_2$ is Br, $R_3$ is H and $R_4$ is —$CH_2$—$OCH_2$—$CH_2OH$;
3. 4-amino-5-iodo-7-(2-hydroxyethoxymethyl)pyrrolo [2,3d]pyrimidine, where $R_1$ is $NH_2$, $R_2$ is I, $R_3$ is H and $R_4$ is —$CH_2$—$OCH_2$—$CH_2OH$;
4. 4-amino-5-chloro-7-[(1,3-dihydroxy-2-propoxy)methyl]pyrrolo[2,3-d]pyrimidine, where $R_1$ is $NH_2$, $R_2$ is Cl, $R_3$ is H and $R_4$ is —$CH_2$—O—$CH(CH_2OH)_2$;
5. 4-amino-5-bromo-7-[(1,3-dihydroxy-2-propoxy)methyl]pyrrolo[2,3-d]pyrimidine, where $R_1$ is $NH_2$, $R_2$ is Br, $R_3$ is H and $R_4$ is —$CH_2$—O—$CH(CH_2OH)_2$;

6. 4-amino-5-iodo-7-[(1,3-dihydroxy-2-propoxy)methyl]pyrrolo[2,3-d]pyrimidine, where $R_1$ is $NH_2$, $R_2$ is I $R_3$ is H and $R_4$ is —$CH_2$—O—$CH(CH_2OH)_2$;

7. 4-amino-5-thiocarboxamide-7-[(1,3-dihydroxy-2-propoxy)methyl]pyrrolo[2,3-d]pyrimidine, where $R_1$ is $NH_2$, $R_2$ is $CSNH_2$, $R_3$ is H and $R_4$ is —$CH_2$—O—$CH(CH_2OH)_2$; and 8. 4-amino-5-thiocarboxamide-7-(2-hydroxyethoxymethyl)pyrrolo[2,3-d]pyrimidine, where $R_1$ is $NH_2$, $R_2$ is $CSNH_2$, $R_3$ is H and $R_4$ is —$CH_2$—$OCH_2$—$CH_2OH$.

B. Method of Use of Compounds

The compounds of the present invention exhibit antiviral activity and acceptable cytotoxicity for use as therapeutic agents. In particular, it has been found that these compounds are effective against HCMV and HSV-1. The compounds are thus useful in the treatment of viral infections caused by the HCMV and HSV-1 viruses as well as other viruses. A partial list of the viruses contemplated to be treatable with the compounds of the present invention includes: herpes simplex virus types 1 and 2; human cytomegalovirus; varicella-zoster virus; Epstein-Barr virus; herpesvirus simian (virus of monkeys); equine herpesvirus-1, 2 and 3; neurolymphomatosis (Marek's disease); influenza viruses A, B and C; parainfluenza viruses-1, 2, 3 and 4; adenovirus; rheovirus; respiratory syncytial virus; rhinovirus; coxsackie virus; echo virus; rubeola virus; hepatitis viruses; and papovavirus.

A compound of the present invention can be used in the treatment of viral infections in animals in accordance with conventional procedures, such as an active ingredient in pharmaceutical compositions, which can be administered topically, or parentally. The pharmaceutical compositions may take the form of tablets, lozenges, granules, capsules, pills, ampoules or suppositories. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

C. Method of Synthesis

1. General Synthesis Schemes

The compounds of the present invention can be synthesized in accordance with the procedures described vide infra. As shown in the following general synthesis Schemes the appropriate pyrrolo[2,3-d]pyrimidine analog can be condensed with an appropriate precursor for the ultimate R groups. This furnishes substituted pyrrolo[2,3-d]pyrimidines which are amenable toward subsequent chemical transformations to afford the requisite compounds. The solvents, reagents and reaction conditions for the preparation of some representative intermediate and target compounds are presented in detail hereinafter.

Scheme 2 -continued

16a, 16b

17a: R = CN
17c: R = CSNH$_2$

18a: R = CN
18c: R = CSNH$_2$

Scheme 3

19

20

21

22a: R = Cl
22b: R = Br
22c: R = I

2. Specific Examples of Chemical Synthesis

The compound numbering in this section refers to the numerals in the above reaction schemes.

a. 4-Chloro-7-(2-acetoxyethoxymethyl)pyrrolo[2,3-d]pyrimidine (3)

Sodium hydride (0.09 g, 60% in mineral oil) was added to a solution of 4-chloropyrrolo[2,3-d]pyrimidine (1) in dry DMF (6 mL) in small portions at 0-5 degrees C under a nitrogen atomosphere. When all hydrogen evolution has ceased, 2-acetoxyethoxymethyl bromide (2) (0.45 g) was added, dropwise with stirring, at room temperature. The reaction mixture was then stirred at room temperature for an additional 3 hours. After that period of time, water (50 mL) was added and the product was extracted with ethylacetate. The ethylacetate layer was separated, washed with cold water, dried over anhydrous, Na$_2$SO$_4$ and the solvent then evaporated under reduced pressure and temperature to afford a thick syrup. This syrup was applied to the top of a silica gel column (20×2 cm) and the column was eluted with 1% MeOH in CHCl$_3$. All the fractions containing UV absorbing material were combined and the solvent from these fractions was evaporated to yield a colorless syrup was crystallized from methanol as colorless needles to yield 0.21 g of 3 (40.2%), mp 67-88 degrees C. $^1$H-NMR (DMSO-d$_6$) δ: 8.5 (s, 1, C2-H), 7.88 (d, 1, J=3.5 Hz, C6-H), 6.72 (d, 1, J=3.6 Hz, C5-H), 5.7 (s, 2, N7-CH$_2$), 4.03 (m, 2, OCH$_2$), 3.52 (m, 2, CH$_2$), 1.92 (s, 3, OAc): UVλ$_{max}$ nm (ε×10$^4$); (pH 7) 223 (1.2), 276 (2.4); (pH 1) 225 (1.2), 274 (0.25); (pH 11) 227 (0.8), 276 (0.2).

Anal. Calcd. for C$_{11}$H$_{12}$N$_3$O$_3$Cl.0.5 MeOH: C, 50.43; H, 5.6; N. 14.711. Found: C, 50.91; H, 5.08; N, 14.43.

b. 4,5-Dichloro-7-(2-hydroxyethoxymethyl)pyrrolo[2,3-d]pyrimidine (7b)

N-Chlorosuccinimide was added to a solution of 4-chloro-7-(2-acetoxyethoxymethyl)pyrrolo[2,3-d]pyrimidine (3) (0.35 g) in dry methylene chloride (15 mL). The reaction mixture was stirred at room temperature for 8 days. At that time, TLC established a complete disappearance of starting material. Water (50 mL) was added to the mixture and the product was extracted with CHCL$_3$ (3×30 mL). The chloroform extracts were combined and washed with water, then dried over anhydrous Na$_2$SO$_4$. The solvent was removed at 40 degrees C in vacuo and the resulting thick syrup was subjected to column chromatography. Elution of the silica gel column (15×2 cm) with benzene: chloroform (1:1), yielded a colorless oil (single spot on TLC) after evaporation of all the UV absorbing fractions at a reduced temperature and pressure, which was crystallized from ethyl alcohol to afford colorless needles of the acetylated intermediate, (7a, 0.23 g) (59.95%). 4,5-Dichloro-7-(2-acetoxyethoxymethyl)pyrrolo[2,3-d]pyrimidine (7a, 0.31 g) was then dissolved in dry methanol (15 mL) and to this solution was added methanol which had previously been saturated with ammonia at 0 degrees C. (25 mL). The reaction mixture was stirred in a pressure bottle at room temperature for 20 hours. The solvent was evaporated at 30 degrees C. in vacuo and the semi-solid mass was subjected to column chromatography. Elution of the product from a silica gel column (15×2 cm) with 2% MeOH in CHCl$_3$ yielded a colorless compound, after evaporation of all the appropriate UV absorbing fractions. This solid was recrystallized from MeOH to furnish 0.11 g of 7. (40.74%), mp 142-143 degrees C.

$^1$H-NMR (DMSO-d$_6$): δ 8.74 (s, 1, C2-H), 8.13 (s, 1, C6-H), 5.66 (s, 2, N7-CH$_2$), 4.65 (t, 1, J=5.3 Hz, exchangeable with D$_2$O, OH), 3.42 (m, 4, CH$_2$): UVλ$_{max}$ nm (ε×10$^4$); (pH 7) 230 (3.3), 271 (0.6), 292 (0.6); (pH 1) 230 (2.8), 292 (0.6); (pH 11) 236 (2.8), 271 (0.4), 294 (0.4).

Anal. Calcd. for C$_9$H$_9$N$_3$O$_2$Cl$_2$: C, 41.22; H, 3.43; N, 16.03. Found: C, 41.29; H, 3.65; N, 15.85.

c. 4-Chloro-5-bromo-7-(2-hydroxyethoxymethyl)pyrrolo[2,3-d] pyrimidine (8b)

A mixture of 4-chloro-7-(2-acetoxyethoxymethyl)-pyrrolo [2,3-d]pyrimidine (3, 0.2 g) and N-bromosuccinimide (0.10 g) was dissolved in dry methylene chloride (10 mL). The reaction mixture was stirred at room temperature for 20 hours. The solvent was evaporated at 40 degrees C. under reduced pressure to give a semi-solid mass which was recrystallized from MeOH as a light brown solid (8a 0.11 g, 50%).

The solid (8a, 0.3 g) was dissolved in dry methanol (10 mL) and to this solution was added methanol saturated with ammonia (20 mL). The reaction mixture was stirred, in a pressure bottle, at room temperature for 20 hours. The solvent was removed at 70 degrees C. under reduced pressure in vacuo and the semi-solid mass was purified by column chromatography. Elution of the silica gel column (15×2 cm) with 2% MeOH in $CHCL_3$ yielded a colorless syrup after evaporation of the appropriate UV absorbing fractions. Trituration of this syrup with ether gave a colorless compound, which was recrystallized from $CHCl_3$ to give 0.11 g of 8b (38.02%), mp 135–136 degrees C. $^1$H-NMR (DMSO-$d_6$): δ 8.72 (s, 1, C2-H), 8.15 (s, 1, C6-H), 5.66 (s, 2, N7-$CH_2$), 4.63 (t, 1, J=5.45 Hz, 3.2 Hz, exhangeable with $D_2O$, OH), 3.46 (m, 4, $CH_2$): UV$\lambda_{max}$ nm ($\epsilon \times 10^4$) (pH 7) 230 (2.5), 270 (0.3), 298 (0.35); (pH 1) 231 (2.7), 270 (0.3); (pH 11) 232 (2.6), 370 (0.3), 301 (0.35).

Anal. Calcd. for $C_9H_9N_3O_2ClBr$: C, 35.24; H, 2.93; N, 13.70. Found: C, 34.77; H, 3.21; N, 13.48.

d. 4-Chloro-5-iodo-7-(2-hydroxyethoxymethyl)pyrrolo[2,3-d] pyrimidine (9b)

Iodine monochloride (0.38 mL) was added dropwise with stirring under a nitrogen atmosphere to a solution of 4-chloro-7-(2-acetoxyethoxymethyl)pyrrolo[2,3-d]pyrimidine (3, 0.82 g) in dry $CH_2Cl_2$ (25 mL). The reaction mixture was stirred at room temperature for 20 hours. The solvent was evaporated at 40 degrees C. under high pressure and the dark purple syrup was placed on the top of a silica gel column. Elution of the column (15×2 cm) with $CHCl_3$ yielded a dark colored syrup, after evaporation of the appropriate UV absorbing fractions, which on trituration with dry ether gave a crystalline product. (0.3 g) as colorless needles. These needles were covered with methanol saturated with ammonia (30 mL) at 0 degrees C., and the reaction mixture stirred at room temperature in a pressure bottle for 20 hours. The solvent was evaporated under high vacuum and the resulting solid was recrystallized from methanol to furnish colorless needles of 9b, 0.21 g (80.75%), mp 154–155 degrees C. $^1$H-NMR (DMSO-$d_6$): 8.69 (s, 1, C2-H), 8.14 (s, 1, C6-H), 5.66 (s, 2, N7-$CH_2$), 4.57 (t, 1, J=3.0 Hz, 3.3 Hz, exchangeable with $D_2O$, OH), 3.46–3.33 (m, 4, $CH_2$): UV$\lambda_{max}$ nm ($\epsilon \times 10^4$); (pH 7) 225 (1.8), 296 (0.9); (pH 1) 233 (2.1), 280 (0.95); (pH 11) 228 (0.8), 280 (0.85).

Anal. Calcd. for $C_9H_9N_3O_2Cl$: C, 30.55; H, 2.54; N, 11.88. Found: C, 30.87; H, 3.00; N, 11.94.

e. 4-Amino-5-chloro-7-(2-hydroxyethoxymethyl)pyrrolo[2,3-d] pyrimidine (10)

4,5-Dichloro-7-(2-hydroxyethoxymethyl)pyrrolo[2,3-d] pyrimidine (7b, 0.07 g) was covered with methanolic-ammonia (20 mL) and heated in a sealed reaction vessel at 135 degrees C. for 10 hours. The solvent was evaporated in vacuo to give a thick syrup. This syrup was subjected to column chromatography and elution of the silica gel column (20×3 cm) with 5% MeOH in $CHCl_3$ furnished colorless needles of 10, after evaporation of the appropriate UV absorbing fractions; 0.04 g. (66.6%), mp 149–150 degrees C. $^1$H-NMR (DMSO-$d_6$): δ 8.14 (s, 1, C2-H), 7.56 (s, 1, C6-H), 6.92 (bs, 2, exchangeable with $D_2O$, $NH_2$), 5.49 (s, 1, N7-$CH_2$), 4.64 (bs, 1, exchangeable with $D_2O$, OH), 3.43 (m, 4, $CH_2$): UV$\lambda_{max}$ nm ($\epsilon \times 10^4$) (pH 7) 214 (2.5), 278 (1.3); (pH 1) 233 (2.8), 280 (1.3); (pH 11) 227 (1.4), 278 (1.3).

Anal. Calcd. for $C_9H_{11}N_4O_2Cl \cdot \frac{1}{4}H_2O$: C, 43.73; H, 4.66; N, 22.67. Found: C, 43.87; H, 4.36; N, 22.23.

f. 4-Amino-5-bromo-7-(2-hydroxyethoxymethyl)pyrrolo[2,3-d] pyrimidine (11)

5-Bromo-4-chloro-7-(2-hydroxyethoxymethyl)pyrrolo [2,3-d]pyrimidine (8b, 0.7 g) was dissolved in dry methanol (10 mL) and methanol saturated with $NH_3$ ammonia (40 mL) was then added to this solution. The reaction mixture was heated at 125 degrees C. in a sealed reaction vessel for 10 hours. The solvent was removed at 40 degrees under reduced pressure and the resulting solid was then subjected to column chromatography. Elution of the silica gel column (20×3 cm) with 5% MeOH in $CHCl_3$ yielded a solid after evaporation of the appropriate UV absorbing fractions. This solid was recrystallized from $CHCl_3$ to afford 11, 0.18 g (31.25%), mp 163–164 degrees C. $^1$H-NMR (DMSO-$d_6$): δ 8.13 (s, 1, C2-H), 7.55 (s, 1, C6-H), 6.81 (bs, 2, exchangeable with $D_2O$, $NH_2$), 5.5 (s, 2, N7-$CH_2$), 4.62 (m, 1, exchangeable with $D_2O$, OH), 3.42 (m, 4, $CH_2$): UV$\lambda_{max}$ nm ($\epsilon \times 10^4$) (pH 7) 211 (1.9), 278 (0.9); (pH 1) 233 (2.0), 280 (0.94); (pH 11) 227 (0.9), 278 (0.95).

Anal. Calcd. for $C_9H_{11}N_4O_2Br$: C, 37.63; H, 3.83; N, 19.51. Found: C, 37.48; H, 3.93; H, 19.77.

g. 4-Amino-5-iodo-7-(2-hydroxyethoxymethyl)pyrrolo[2,3-d] pyrimidine (12)

4-Chloro-5-iodo-7-(2-hydroxyethoxymethyl)pyrrolo[2,3-d] pyrimidine (9b, 0.3 g) was covered with methanol saturated with ammonia (25 mL) and the reaction mixture was heated at 130 degrees C. in a sealed vessel for 10 hours. The solvent was concentrated in vacuo to give a semi-solid mass which was recrystallized from methanol to afford 12, 0.20 g (71.4%), mp 169–170 degrees C. $^1$H NMR (DMSO-$d_6$): δ 8.7 (s, 1, C2-H), 8.3 (s, 1, C6-H), 5.7 (s, 2, N7-$CH_2$) 4.6 (t, 1, J=4$H_3$, exchangeable with $D_2O$, OH): UV$\lambda_{max}$ nm($\epsilon \times 10^4$); (pH 7) 210 (2.0), 280 (0.9); (pH 1) 230 (1.8), 279 (0.9); (pH 11) 228 (0.9), 278 (0.9).

Anal. Calcd. for $C_9H_{11}N_4O_2I$; C, 32.43; H, 3.30; N, 16.81. Found: C, 32.49; H, 3.58; N, 16.70.

h. 4-Amino-5-cyano-7-(2-hydroxyethoxymethyl)pyrrolo[2,3-d] pyrimidine (17a):

4-Amino-6-bromo-5-cyanopyrrolo[2,3-d]pyrimidine (2.38 g, 10 mmole) was dissolved in dry DMF (40 mL). Sodium hydride (97%) (0.25 g, 10 mmol) was added to this solution (at 100 degrees) under a nitrogen atmosphere, and the solution was stirred for 30 minutes. 2-Acetoxyethoxymethyl bromide (1.98 g; 10 mmole)

was added to this solution with stirring, and the reaction mixture heated at 100 degrees for an additional 6 hours. The solution was concentrated in vacuo, and the residue partitioned in a mixture of EtOAc:H$_2$O (2×20 mL), and dried over Na$_2$SO$_4$. The ethyl acetate was evaporated, absorbed onto silica gel (8 g), and chromatographed on a silica gel column (2×80 cm) using silica gel (120 g; 60–200 mesh). Elution of the column with CH$_2$Cl$_2$:CH$_3$OH (97:3) gave the desired nucleoside 15a. $^1$H NMR (DMSO-d$_6$): δ 5.65 (s, 2H, C$_1'$—CH$_2$), 7.05 (bs, 2H, NH$_2$), 8.30 (s, 1H, C$_2$—H. Further elution of the column with the same solvent CH$_2$Cl$_2$:CH$_3$OH (97:3) gave compound 15b. $^1$H NMR (DMSO-d$_6$): δ 5.72 (s, 2H, C$_1'$—CH$_2$), 8.65 (s, 1H, C$_2$—H). This provided a combined yield of 2.3 g (yield 65%).

A mixture of 15a and 15b (1.77 g; 5 mmole) was dissolved in a mixture of abs. EtOH and EtOAc (1:1; 60 mL). To this solution, 5% Pd-C (2.0 g) and basic MgO (1.7 g) was added and the mixture hydrogenated at 48 psi for 12 hours. The reaction mixture was filtered through a Celite pad. The filtrate was evaporated to dryness, this was absorbed onto silica gel (5.0 g), and then chromatographed on a silica gel column (2×60 cm) using silica gel (80 g; 60–200 mesh). Elution of the column with CH$_2$Cl:CH$_3$OH (96:4) gave the desired nucleoside 16a (0.6 g; yield 43.79%); m.p. 138 degrees C.; $^1$H NMR (DMSO-d$_6$): δ 1.95 (s, 3H, COCH$_3$), 3.70 (m, 2H, CH$_2$), 4.05 (m, 2H, CH$_2$, 5.6 (s, 2H, C$_1'$—CH$_2$), 6.95 (bs, 2H, D$_2$O exchangeable, NH$_2$), 8.39 (s, 1H, C$_6$—H), 8.42 (s, 1H, C$_2$—H), 8.42 (s, 1H, C$_2$—H). IR(KBr): 3440, 2120, 1740 cm$^{-1}$.

Anal. Calcd. for C$_{12}$H$_{13}$N$_5$O$_3$: C, 52.36; H, 4.76; N, 25.44. Found: C, 52.49; H, 4.60; N, 25.17.

Further elution of the column furnished 16b (0.4 g; yield: 29.09%); m.p. 136–37 degrees C.; $^1$H NMR (DMSO-d$_6$): δ 1.95 (s, 3H, COCH$_3$), 3.85 (m, 2H, CH$_2$), 4.10 (m, 2H, CH$_2$), 5.75 (s, 2H, C$_1'$—CH$_2$), 8.85 (s, 1H, C$_6$—H), 9.50 (s, 1H, C$_2$—H).

Conversion of 16b to 16a:

Compound 16b (0.3 g) was dissolved in dry toluene (50 mL), molecular sieve (3A degrees; 1.0 g) was added and the solution heated at reflux under stirring for 36 hours. The mixture filtered, and the filtrate concentrated in vacuo. The residue was purified by filtering through a small column of silica gel. The desired fractions were combined, concentrated, and the residue was crystallized from abs. EtOH to give 16a (0.22 g; yield 73%).

Compound 16a (0.69 g; 2.5 mmole) was stirred with methanolic NH$_3$ (saturated at 0 degrees C.; 30 mL), in a pressure bottle at 5 degrees C. for 6 hours. At this point, TLC showed the absence of any starting material. The solution was absorbed onto silica gel (5.0 g), and the product was purified by passing through a column chromatography of silica gel (column size 2×80 cm; silica gel 80 g; 60–200 mesh). Elution of the column with CH$_2$Cl$_2$:CH$_3$OH (95:5) gave the desired nucleoside 17a, which was crystallized from abs. EtOH to get 9 (0.25 g; yield 43.1%); m.p. 178 degrees C.; UVλ$_{max}$ nm: MeOH, 278 (4610); pH 1, 235 (6200), 270 (6200); pH 11; 216 (28800), 277 (4644); IR(KBr): 3460, 2205, 1660 and 1600 cm$^{-1}$. $^1$H NMR (DMSO-d$_6$): δ 3.47 (m, 4H, CH$_2$), 4.65 (t, 1H, D$_2$O exchangeable, OH), 5.57 (s, 2H, C$_1'$—CH$_2$), 6.87 (bs, 2H, NH$_2$), 8.25 (s, 1H, C$_6$—H), 8.34 (s, 1H, C$_2$—H).

Anal. Calcd. for C$_{10}$H$_{11}$N$_5$O$_2$: C, 51.49; H, 4.75; N, 30.02. Found: C, 51.31; H, 4.81 and N, 29.86.

D. EXAMPLES OF TESTING AND USE OF COMPOUNDS

Figure 1:
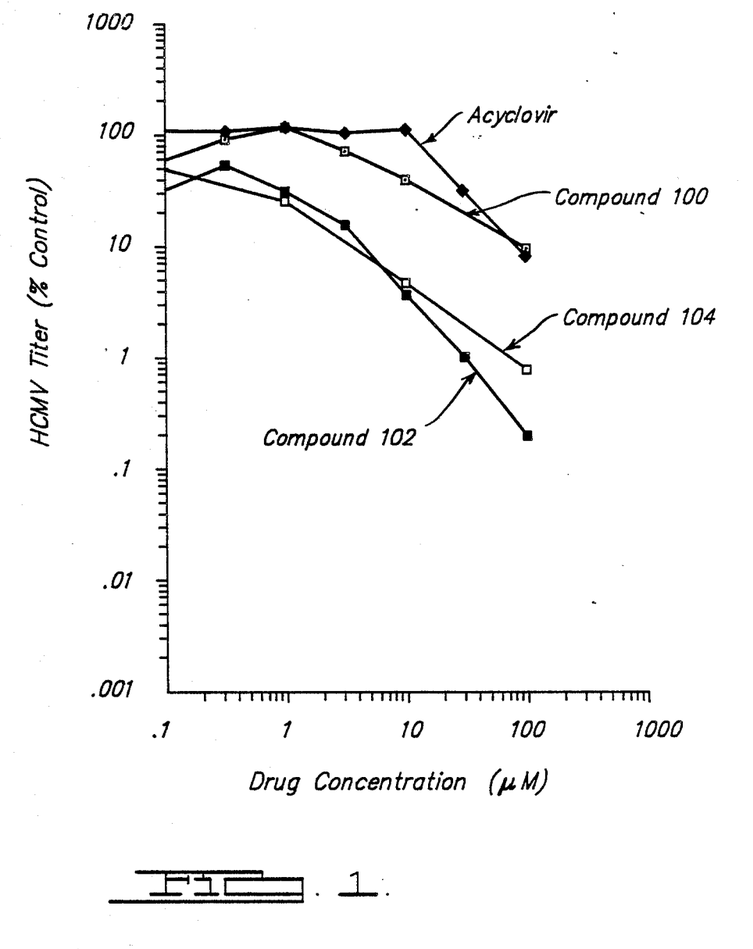
FIGS. 1 and 2 are graphs showing HCMV titer reduction by antiviral compounds.
Figure 2:
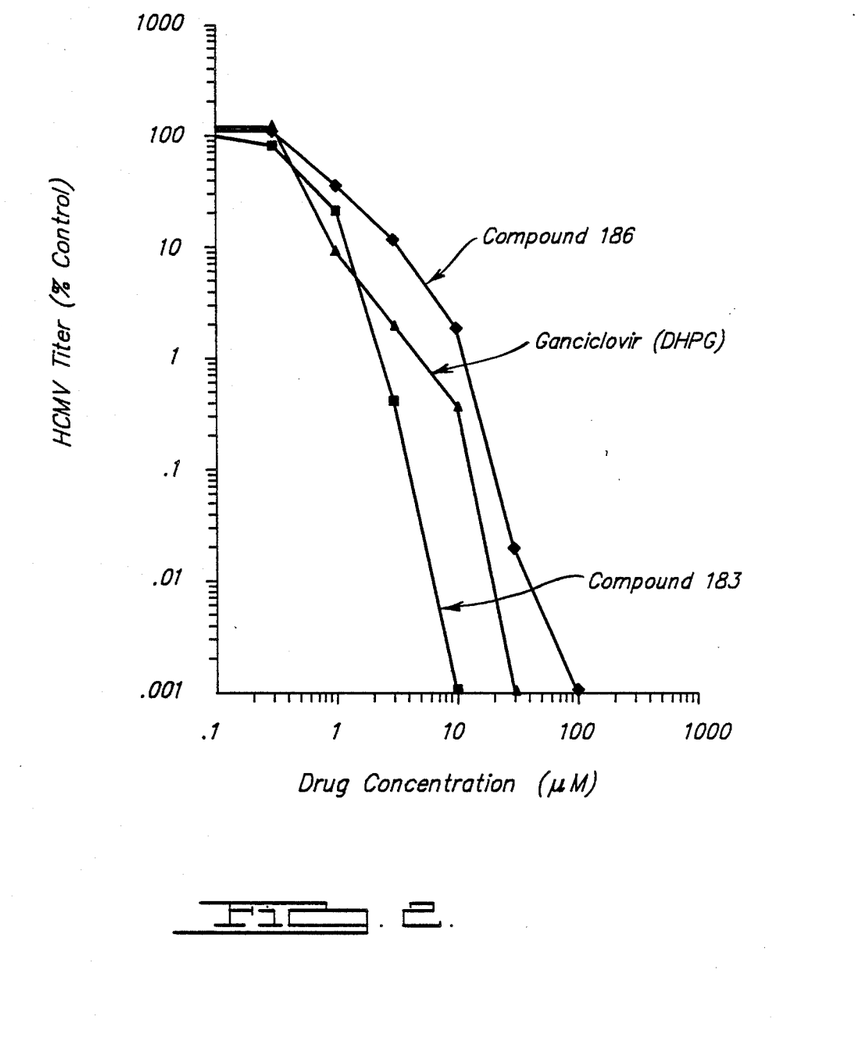

The following test methods were followed in generating the data in Tables 1 and 2 and FIGS. 1 and 2:

1. Methods a. Propagation of Cells and Viruses (1) Cells

The routine growth and passage of KB cells—a human epidermoid neoplastic cell line—was performed in monolayer cultures using minimal essential medium (MEM) with either Hanks salts [MEM(H)] or Earl salts [MEM(E)] supplemented with 10% calf serum or 5 to 10% fetal bovine serum. The sodium bicarbonate concentration was varied to meet the buffering capacity required. BSC-1 (African green monkey kidney) cells were grown and passaged in Dulbecco modified MEM(E) supplemented with 5% tryptose phosphate broth and 5% horse serum. Cultures of diploid human foreskin fibroblasts (HFF) were grown in medium consisting of MEM(H) with 10% fetal bovine serum.

Cells were passaged and 1:2 to 1:10 dilutions according to conventional procedures by using 0.05% trypsin plus 0.02% EDTA in a HEPES buffered salt solution. HFF cells were passaged only at 1:2 dilutions.

(2) Viruses

The 148 strain of HSV-1 was used in most experiments and was provided by Dr. T. W. Schafer of Schering Corporation. The HF strain of HSV-1 was used in selected experiments and was obtained from Dr. G. H. Cohen, University of Pennsylvania. The Towne strain, plaque-purified isolate P$_o$, of HCMV was a gift of Dr. Mark Stinski, University of Iowa.

High titer HSV-1 stocks have been prepared as follows: Nearly confluent monolayer cultures of KB cells were grown in 32 oz. glass bottles containing MEM(E) buffered with 25 mM HEPES and supplemented with 5% fetal bovine calf serum and 0.127 gm/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min). The cell pellet was resuspended in 1/40 of the original volume of medium and disrupted by three cycles of freezing and thawing. The resulting virus pools were stored at −76° until retrieved for use in experiments.

Stock HCMV was prepared by infecting HFF cells at a multiplicity of infection (m.o.i.) of less than 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HSV-1 was titered using monolayer cultures of BSC-1 cells. Cells were planted at 3×10$^5$ cells/well using 6-well cluster dishes. MEM(E) supplemented with 10% fetal bovine serum was employed as medium. After 22–24 hours, cells were 90% confluent and were inoculated in triplicate using at least three one-logarithm dilutions with 0.2 ml of the virus suspension to be assayed and incubated in a humidified 4% CO$_2$-

90% air atmosphere for one hour to permit viral adsorption. Following virus adsorption, the cell sheet was overlaid with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

HCMV was titered in 24-well cluster dishes which were planted to contain $5 \times 10^4$ HFF cells/well, grown as described above. When the cells were 70 to 80% confluent, 0.2 ml of the virus suspension was added per well and adsorbed as described above. At least three one-logarithm dilutions of each preparation were used. Following virus adsorption, the cell sheets were overlaid with 0.5% methocel (4000 CPS) in maintenance medium [MEM(E) with 1.1 gm/liter $NaHCO_3$, 100 units/ml penicillin G, 100 μg/ml streptomycin, and 5% fetal bovine serum]. The cultures were incubated in a humidified atmosphere of 4% $CO_2$-96% air. Viral foci were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

b. Assays for Antiviral Activity (1) HSV-1

Plaque reduction experiments with HSV-1 were performed using monolayer cultures of BSC-1 cells. The assay was performed exactly as described above except that the 0.2 ml virus suspension contained approximately 100 p.f.u. of HSV-1. Compounds to be tested were dissolved in the overlay medium at concentrations usually ranging from 0.1 to 100 μM in half-or-one logarithm dilutions. Titer reduction assays were performed by planting KB cells in 25 cm² plastic tissue culture flasks 10 to 24 hours prior to infection. At the onset of experiments, logarithmically growing replicate monolayer cultures were 60 to 80% confluent and contained 2.5 to $4.5 \times 10^6$ cells/flask. Medium was decanted and the cultures were infected with 2 to 10 p.f.u. of HSV-1 per cell. Virus was contained in 1.0 ml of VGM supplemented with 5% fetal bovine serum. After a 1 hour adsorption period at 37° C., the cell sheet was rinsed twice with 2 ml of VGM without serum to remove unadsorbed virus and 5 ml of VGM containing drugs at three to five selected concentrations added in duplicate. Following an 18- to 22- hour incubation at 37° C., infected monolayers was or treated with EDTA-trypsin to suspend the cells; aliquots were removed, subjected to three cycles of freezing and thawing, and stored at −76° C. for subsequent virus assay. Virus was titered on BSC-1 cells as described above.

Drug effects were calculated as a percentage of the reduction in virus titers in the presence of each drug concentration compared to the titer obtained in the absence of drug. Acylovir was used as a positive control in all experiments.

(2) HCMV

The effect of compounds of the replication of HCMV has been measured using both a plaque (focus) reduction assay and a titer (yield) reduction assay. For the former, HFF cells in 24-well culture dishes were infected with approximately 50 p.f.u. of HCMV per cm² cell sheet using the procedures detailed above. Compounds dissolved in growth medium were added in three to six selected concentrations to triplicate wells following virus adsorption. Following incubation at 37° C. for 7 to 10 days, cell sheets were fixed, stained and microscopic foci were enumerated as described above. Drug effects were calculated as a percentage of reduction in number of foci in the presence of each drug concentration compared to the number observed in the absence of drug. DHPG (ganciclovir) has been used as a positive control in all experiments.

For titer reduction assays, HFF cells were planted as described above in 24-well cluster dishes or in 25 cm² flasks. When monolayers were approximately 70% confluent, HCMV was added at a m.o.i. of 0.5 p.f.u. per cell and adsorbed as detailed above. Compounds dissolved in growth medium were added in one or one-half-logarithm dilutions and incubation continued at 37° C. After 7 to 10 days of incubation, culture dishes or flasks were frozen at 76° C. For titer determination, cells were thawed and then subjected to two more cycles of freezing and thawing at 37° C. Serial, one-logarithm dilutions of the final suspension were prepared and incculated onto new cultures of HFF cells. Titer determination was as detailed above in part lb.

c. Cytotoxicity Assays (1) Protocol for Determining Effects of DNA, RNA and Protein Synthesis KB or HFF cells were planted using a Costar Transplate-96 (Costar, Cambridge, Massachusetts) in Costar 96-well cluster dishes at a concentration of 10,000 to 12,000 cells per well. Wells were suspended in 200 μl of medium [MEM(H) plus 0.7 gm/liter $NaCHO_3$ supplemented with 10% calf serum] per well. After incubation of 16 to 24 hours at 37° C. in a humidified atmosphere of 4% $CO_2$ in air, 150 μl of medium was removed per well. One-hundred μl of medium with or without compounds in twice their final concentrations was added to each well using a Titertek Multichannel Pipette. Final concentrations of compounds ranged from 0.1 to 320 μM. fifty μl of medium containing radioactive precursors also was added to each well to give a final concentration to 1 to 3 UCi/ml of labeled precursor. [$^3$H] Thd was diluted with unlabeled d Thd to give a final concentration of 3 or 6 μM.

Following addition of drugs and labeled precursors, plates were incubated as described above for an additional 18 to 24 hours. Logarithmic cell growth occurred during this time with continual uptake of labeled precursors. At the end of the incubation period, cells were individually harvested from each well using a Skatron Cell harvester (Skatron, Inc., Sterling, Virginia). Cultures for individual wells were harvested onto filter paper and washed free of unincorporated label with nine sequential washes with 5% trichloroacetic acid, nine washes with water, and nine with ethanol using the Skatron unit. Filters were dried, circles from individual cultures were punched from the filter mat and placed into mini-vials. Liquid scintillation solution was added, and radioactivity determined in a Beckman model LS8100 liquid scintillation spectrometer. All samples were counted for 2.0 minutes each, time three rounds of counting. Counts per minute were determined following the application of statistical methods to eliminate count rates which fell outside distribution limits defined by Chauvenet's rejection criterion.

All analyses were performed in triplicate. That is, three culture wells were used per time point, radioactive precursor, and drug concentration in all experiments. Results from triplicate assays were converter to percent of control and plotted as log dose-response curves from which 50% inhibitor ($I_{50}$) concentrations were interpolated. Three concentrations of vidarabine were included on all plates as a positive control.

(2) Visual Scoring

Cytotoxicity produced in HFF and BSC-1 cells has been estimated by visual scoring of cells not affected by virus infection in the HCMV and HSV-1 plaque reduction assays. Cytopathology was estimated at 35- and 60-fold magnification and scored on a zero to four plus basis. Wells were scored on the day of staining.

d. Cell Growth Rates

Population doubling times and cell viability were measured in uninfected HFF and/or KB cells. Cells were planted in replicate 6-well plastic tissue culture dishes or in 25 cm$^2$ flasks as described above in part 1. Following an incubation period during which cells attached to the substrate, medium was decanted, the cell sheet rinsed once with HBS, and fresh medium added. The medium consisted of MEM(E) with 1.1 gm NaHCO$_3$/liter and 10% fetal bovine or calf serum plus appropriate log or half-log concentrations of drug. After additional periods of incubation from 1 to 72 hours at 37° C., cells were harvested by means of 0.05% trypsin plus 0.02% EDTA in a HEPES-buffered salt solution. Cells were enumerated using either a Coulter counter or a hemocytometer and viability determining using trypsan blue dye exclusion.

e. Plating Efficiency

A plating efficiency assay was used to confirm and extend results described above. Briefly, KB cells were suspended in growth medium and an aliquot containing 1000 cells was added to a 140×25 mm petri dish. Growth medium (40 ml) containing selected concentrations of test compounds was added and the cultures incubated in a humidified atmosphere of 4% CO$_2$-96% air, 37° C. for 14 days. Medium then was decanted and colonies fixed with methanol and stained with 0.1% crystal violet in 20% methanol. Macroscopic colonies greater than 1 mm in diameter were enumerated. Drug effects were calculated as a percentage of reduction in number of colonies formed in the presence of each drug concentration compared to the number of colonies formed in the absence of drugs. Dose-response curves were generated and $I_{50}$ concentrations for inhibition of plating/colony formation were calculated.

f. Flow Cytometry (1) Preparation of KB Cells and Nuclear DNA Staining

Untreated and drug-treated cultures of KB cells in 6-well plates were harvested and resuspended in MEM(E) plus 5% fetal bovine serum as previously described. See S. R. Turk, C. Shipman, Jr., M. R. Nassiri, G. Genzlinger, S. Krawczyk, L. B. Townsend and J. C. Drach, *Antimicrob. Agents Chemother.*, 31:544, 1987. Aliquots of the cells were placed into test tubes at a concentration of $3 \times 1^{-5}$ cells/ml. Chicken erythrocytes and human lymphocytes in amounts equal to 20% of the KB cells were added as internal biological standards. Samples were centrifuged in a Beckman model TJ-6 at 200X g for 5 minutes. The supernatants were decanted and vortexed gently to resuspend pellets. One ml of phosphate-buffered saline was added per tube and the tubes were centrifuged as described above.

The staining solution used for flow cytometric analysis was a modification of Vindelov's procedure. See L. L. Vindelov, *Virchow's Arch. Cell Pathol.*, 24:227, 1987. Staining solution contained 0.01M Trisma base, 700U/liter RNase, 0.1% nonident P40 (NP40), 10 mM sodium chloride and $7.5 \times 10^{-5}$M propidium diiodide (PI). One ml PI reagent was added to each test tube and vortexed gently. The resulting nuclear preparation was placed on ice/water for 30 minutes. After incubation, the nuclear suspensions were fixed by addition of 100 μl paraformaldehyde per tube, vortexed, and stored in the dark at 4° C. overnight until ready to run on the flow cytometer.

(2) Flow Cytometry

PI-stained nuclei were analyzed on an EPOCS V flow cytometer (Coulter Electronics, Miami, Florida) fitted with an argon-ion laser emitting at 488 nm (400 mW), and with a 515 nm long pass filter, 560 nm dichroic filter, 630 nm long pass filter (red, DNA). Photomultiplier tube high voltage was adjusted to maintain the chick erythrocyte (CRBC) peak in channel 20. The CRBC also served as a threshold for acceptable fluorescence intensity; events having less fluorescence than CRBC nuclei were considered debris. In all samples, a total of 10,000 nuclei were analyzed.

(3) Analysis of DNA Histograms

Data storage and analyses, which included smoothing, translocation, are normalization, averaging of histograms and statistical comparisons (nonparametric analysis), were done by using the Coulter EASY Computer system. For comparisons, the CRBC peaks were translocated to channel 20. Therefore, fluorescence from human lymphocytes (2C; G0=G1) and untreated as well as treated KB cells was located between channels 55 and 105 respectively. All histograms are averages of five histograms from the same test group. A channel-by-channel Gossett (student's t-test was performed (p less than 0.05) and is displayed as vertical lines underneath the main histograms.

g. Viral DNA Determination by "Dot-Blot" Hybridization

The amount of HCMV DNA synthesis has been determined in two types of experiments: (a) as an integral part of HCMV titer (yield) reduction experiments and (b) as separate experiments to determine only the amount of viral DNA synthesis in the absence or presence of test compounds.

(1) Determination in Titer Reduction Experiments

HFF cells were planted in 25 cm$^2$ flasks and infected with HCMV as described in part 2 and incubated at 37° C. Before harvesting at selected times by the addition of 0.1 volume of 0.2M EDTA, an aliquot of medium was removed for determination of HCMV titer. After harvesting cells into the medium, aliquots were retained for determination of HCMV DNA by hybridization.

(2) Determination of HCMV DNA in Microtiter Plate Cultures

HFF cells were planted in 96-well cluster plates at 20,000 cell/well in 200 μl of growth medium [MEM(E)] with 1.1 gm/liter NaHCO$_3$ and 10% fetal bovine serum. After incubation in a humidified atmosphere of 4% CO$_2$-96% air for 1 to 2 days, growth medium was aspirated and the 70% confluent cells were infected at a m.o.i. of 0.5 p.f.u. per cell by addition of HCMV in 100 μl of MEM(E) with 1.1 gm/1 liter NaHCO$_3$ and 5% fetal bovine serum (maintenance medium). Following a 1-hour incubation at 37° C. for virus adsorption, 100 μl of selected concentrations of test compounds were added to each of triplicate wells in twice their final concentration of maintenance medium. Usually 3 to 6 concentrations of compounds were tested in 3.2- or 10-fold dilutions along with appropriate triplicate no drug and no virus controls. Plates were incubated for 7 days and harvested by addition of 100 μl of 0.25M EDTA per well. After a 30-minute incubation of 37° C. to free the cells, the contents of the wells were filtered as described below or frozen at −76° C. for subsequent analysis. The following procedure adapted from H. Gadler, *Antimicrob. Agents Chemother.*, 24:370, 1983 was employed for the hybridization portion of the assay:

(1) The contents of each well were removed and filtered through Gene Screen ™ (NEN Research Products), presoaked in 10×SSC (1×SSC is 0.15M NaCl, 0.015M NaCitrate), using a 96-well filtration manifold (Schleicher and Schuell).

(2) The original microtiter plate wells were rinsed with 200 μl HEPES buffered saline and the contents added to the filter manifold.

(3) The Gene Screen membrane was dried at room temperature and then baked at 80° to 100° C. for 3 to 4 hours.

(4) The DNA on the membrane was denatured by placing the membrane (sample side up) sequentially on filter papers soaked in (a) 0.5M NaOH for 30 minutes, (b) 0.1M NaOH, 1.5M NaCl for 5 minutes, (c) 1M Tris CHl, pH 7.5 twice each fro 5 minutes, (d) 0.5M Tris HCl, pH 7.5, 1.5M NaCl for 5 minutes and then dried at room temperature.

(5) The membrane was added to a "hybridization bag" and prehybridized at 65° C. for (greater or equal to) 6 hours in 10 ml 0.2% polyvinylpyrrolidone (MW 40,000); 0.2% ficoll (MW 400,000); 0.2% bovine serum albumin; 0.05M Tris HCl, pH 7.5; 0.1% sodium pyrophosphate; 1M NaCl; 10% dextran sulfate (ME 500,000) and 0.1 mg/ml denatured salmon testes DNA.

(6) 1.1 μg of radioactively-labeled DNA probe was added to the prehybridization mixture and incubated overnight at 65° C. (The probe is plasmid pACYC-184, containing Xba I fragment 1c of HCMV. It was amplified in E. coli HB101, rec A- provided through the courtesy of Dr. Mark Stiriski, University of Iowa. The probe was nick translated with [$^{32}$P]dCTP using a kit obtained from Cooper Biomedical, denatured, and used directly for hybridization).

(7) Following hybridization, the membrane was washed sequentially in 100 ml 2×SSC at room temperature twice each for 5 minutes, 100 ml 2×SCC plus 1% SDS at 65° C. twice each for 30 minutes and then 100 ml 0.1×SSC at room temperature twice each for 30 minutes.

(8) The membrane was dried at room temperature and each filtration spot was cut from the membrane and placed into 4 ml of toluene/DPO scintillant and hybridized label counted in a liquid scintillation spectrometer.

h. Data Analysis

Dose-response relationships were used to compare drug effects. These were constructed by linearly regressing the percent inhibition of parameters derived in the preceding sections against log drug concentrations. The 50% inhibitory ($I_{50}$) concentrations were calculated from the regression lines using the methods described by Goldstein. See A. Goldstein, *Biostatistics: An Introductory Text*, MacMillan, New York, 1064, pp. 156–161. The three $I_{50}$ concentrations for inhibition of DNA, RNA, and protein synthesis were averaged and were reported in the tables. Along with the $I_{50}$ concentration for visual cytotoxicity, the averaged $I_{50}$ concentrations are compared to $I_{50}$ concentrations for inhibition for HCMV or HSV-1 replication. Compounds for which the ratio of cytotoxicity $I_{50}$ concentrations to antiviral $I_{50}$ concentrations (in vitro therapeutic index) were greater than 10, were considered for further study.

2. Results

Test results are set forth in the following Tables 1 and 2.

TABLE 1

Antiviral Activity and Cytotoxicity of 4,5-Substituted 7-Acyclic Pyrrolo[2,3-d]pyrimidines.

| Compound | | | | | 50% Inhibitory Concentration (μM) | | | | | | |
|---|---|---|---|---|---|---|---|---|---|---|---|
| UMJD | | Substituent | | | HCMV | | HSV-1$^r$ | | Cytotoxicity | | |
| No.$^a$ | No.$^b$ | 4 | 5 | 7$^v$ | Plaque | Yield$^p$ | Plaque | Yield$^p$ | HFF$^c$ | BSC$^c$ | KB$^d$ |
| *Acyclovir*$^e$ | | | | HEM | 63 | 90 | 4 | 7 | >100 | >100 | >100 |
| *Ganciclovir (DHPG)*$^e$ | | | | DHPM | 8.8$^{h(23)}$ | 1.8 | 4.5 | | >100$^{h(23)}$ | >100 | 1000 |
| 10 | 100 | NH$_2$ | Cl | HEM | 16.$^{h(4)}$ | 46$^{h(3)}$ | 77 | 50 | >100$^{h(4)}$ | >100 | 350$^{h(5),t}$ |
| 11 | 102 | NH$_2$ | Br | HEM | 3.9$^{h(5)}$ | 13$^{h(3)}$ | 11$^{h(2)}$ | 40 | 100$^{h(5)}$ | >100$^{h(2)}$ | 100$^{h(5),t}$ |
| 12 | 104 | NH$_2$ | I | HEM | 24.$^{h(3)}$ | 14$^{h(3)}$ | 250 | >100 | 100$^{h(2)}$ | >100 | 94$^{h(2),t}$ |
| 22a | 186 | NH$_2$ | Cl | DHPM | 9.8$^{h(2)}$ | 8$^{h(2)}$ | 16 | | >100$^{h(2)}$ | >100 | >100$^t$ |
| 22b | 183 | NH$_2$ | Br | DHPM | 1.6$^{h(2)}$ | 1.9$^{h(2)}$ | 2 | | >100$^{h(2)}$ | >100$^{h(2)}$ | 25 |
| — | 239 | NH$_2$ | CSNH$_2$ | DHPM | 8.0$^{h(2)}$ | 25 | — | — | >100$^{h(2)}$ | — | >100$^t$ |

TABLE 2

Antiviral Activity and Inhibition of Viral DNA Synthesis 4,5-Substituted 7-Acyclic Pyrrolo[2,3-d]pyrimidines.

TABLE 2-continued

| Name | Compound UMJD No.[a] | No.[b] | Substituent 4 | 5 | 7[y] | 50% Inhibitory Concentration (μM) HCMV Titer, Plaque or Yield Reduction | HCMV DNA Synthesis |
|---|---|---|---|---|---|---|---|
| *Acyclovir*[e] | | | | | HEM | 63 | 35 |
| *DHPG*[e] | | | | | DHPM | 8.8[h(23)] | 1.1[h(4)] |
| Compound 100 | 112 | 100 | $H_2N$ | Cl | HEM | 16[h(4)] | 15[h(3)] |
| Compound 102 | 111 | 102 | $H_2N$ | Br | HEM | 3.9[f,h(5)] | 3.2[h(3)] |
| Compound 104 | 113 | 104 | $H_2N$ | I | HEM | 24[h(3)] | 47[h(2)] |

FOOTNOTES TO TABLES 1-2
[a]Number for chemical structure presented in text.
[b]Identification number assigned to compounds provided to Drach from Townsend.
[c]Visual cytotoxicity scored on HFF or BSC-1 cells at time of HCMV or HSV-1 plaque enumeration.
[d]Average percent inhibition of DNA, RNA and protein synthesis determined in KB cells as described in the text.
[e]Known antiviral drugs. Acyclovir is marketed under the brand name 'Zovirax'.
[h]Average $I_{50}$ concentration derived from (. . .) experiments.
[p]90% inhibitory concentration ($I_{90}$) presented
[f]Results with HSV-1 strain S-148. $I_{50}$ with HF strain = 36, >100, 28, 54 μM for acyclovir, compounds 100, 102 and 104 respectively.
[i]Effect on [$^3$H]Urd and $^3$H-amino acid incorporation only. The following effects were observed on [$^3$H]dThd incorporation:

| Compound | $I_{50}$ |
|---|---|
| 100 | 0.82 |
| 102 | 0.13 |
| 104 | 1.2 |
| 186 | 28 |
| 239 | 23 |

[y]Abbreviations used are DHPM: (dihydroxypropoxy)methyl; HEM: (hydroxyethoxy)methyl.

a. Antiviral Activity and Cytotoxicity of 7-[(hydroxyethoxy) methyl]-pyrrolo[2,3-d]pyrimidines (HEM nucleosides)

The 4-amino-5-Cl-, 5-Br-, and 5-I-7-[(2-hydroxyethyoxy)methyl]pyrrolo[2,3-d]pyrimidines (compounds UMJD No. [b] 100, 102, 104, respectively, also shown in the Tables as compounds No. [a] 10, 11, 12, but hereinafter referred to by their UMJD No. [b]) were active against HCMV. This activity was quite surprising because the related compound, acyclovir, has only modest activity against HCMV (Tables 1 and 2). Similar but less potent activity also was found against herpes simplex virus type 1 (HSV-1) (Tables 1 and 2).

All compounds produced only little visual cytotoxicity in HFF cells and affected [$^3$H]Urd and $^3$H-amino acid incorporation in KB cells only at concentrations over 100 μM. All three 4-amino compounds were potent inhibitors of [$^3$H]dThd incorporation ($I_{50}$ less than 1 μM). The later may be misleading, however, because when DNA was labeled with inorganic phosphate, the $I_{50}$ was approximately 10 μM. A similar circumstance exists with ribavirin where [$^3$H]dThd incorporation seriously overestimates inhibition of cellular DNA synthesis. See J. C. Drach, M. A. Thomas, J. W. Barnett, S. H. Smith and C. Shipman, Jr., Science, 212:549, 1981. When labeled precursor experiments were repeated in HFF cell, the Cl- and Br-compounds inhibited [$^{32}$P]phosphate labeling of DNA by only 10% at 100 μM. Because of these interesting observations, secondary tests were performed.

FIG. 1 and Table 1 illustrate the effects of the halogen compounds on HCMV in titer reduction assays. The compounds required 32 to 100 μM concentrations to give a 2-3 log reduction in virus titer. These results for compounds UMJD 102 and 1-4 are approximately 10-fold better than for the known antiviral drug acyclovir (FIG. 1).

In more extensive cytotoxicity testing, the compounds were tested for effects on the growth of KB cells. Populations doubling times were calculated from the logarithmic portions of growth curves and are as follows:

| Drug Concentration (μM) | Population Doubling time (hr) in the Presence of | | |
|---|---|---|---|
| | UMJD 100 (5-Cl) | UMJD 102 (5-Br) | UMJD 104 (5-I) |
| 0.0 | 23 | 23 | 23 |
| 0.1 | ND | 30 | 26 |
| 1.0 | 25 | 43 | 25 |
| 10.0 | 25 | 84 | 30 |
| 100.0 | 27 | ND | ND |

As can be seen, the 5-Cl compound affected KB cell growth to only a minor extent even at a concentration of 100 μM. The effect of these compounds on the growth of human diploid fibroblasts (HFF cells) was less pronounced. During a 70-hour incubation, control cells underwent two doublings. In the presence of 10 or 32 μM compounds' UMJD 100) there was no decrease in the number of cells present at 70 hours. A 100 μM concentration reduced the number of cells by less than 10%. The effects of the Br and I compounds UMJD 102, UMJD 104, respectively, were more pronounced. Nonetheless, cells still underwent one population doubling in 70 hours in the presence of 100 μM concentrations of either compound. Compound UMJD 100 also did not affect DNA synthesis in human PBLs stimulated by pokeweed mitogen or concanavalin A at concentrations of 0.1, 1, 10 and 100 μM. Additional tests indicated that these compounds are cytostatic, not cytotoxic. See J. C. Drach and L. B. Townsend, First semi-annual technical progress report for Contract Number NO1-AI-72641 to the Public Health Service, National Institute for Allergy and Infectious Diseases, National institute of Health, Bethesda, Maryland 20892, March, 1988.

The effects of the three halogen compounds on HCMV DNA synthesis were also measured. Inhibition of viral DNA synthesis occurred at levels slightly lower than those required for inhibition of virus replication (Table 2). We interpret these results to mean that the compounds may act by inhibiting viral DNA synthesis.

b. Antiviral Activity and Cytotoxicity of 7-[(Dihydroxypropoxy)methyl]-pyrrolo[2,3-d] pyrimidines (DHPM nucleosides)

Results with the Cl- and Br- analogs in the DHPM series were more dramatic. FIG. 2 shows that the Br-compounds (UMJD 183) reduced HCMV titers by nearly 5 logs (100,000-fold) at 10 μM. This is more potent than the known antiviral drug ganciclovir. The Cl compound (UMJD 186) also produced a 5-log reduction in virus titer but required a 10-fold higher concentration.

As discussed above, the Br-compound in the HEM series (UMJD 102) is cytostatic. Concentrations as low as 0.1 μM inhibited the growth of KB cells. When similar experiments were performed with the Br-compound in the DHPM series (UMJD 183), growth of KB cells was also inhibited, but to a lesser extent. Cell growth occurred to 20 hours in the presence of drug before slowing or stopping. In separate experiments, growth occurred in the presence of up to 32 μM drug for 50 hours, but at a reduced rate.

What is claimed is:

1. A compound selected from the group consisting of compounds of the following formula and pharmaceutically acceptable salts thereof:

where
$R_1$ is $NH_2$ or NHOH;
$R_2$ is $CSNH_2$, Cl, Br, I, F, 2-buten-1-yl, 5-(1-hydroxyethyl) or 5-(1-methoxyethyl);
$R_3$ is H, $NH_2$ or Br; and
$R_4$ is (1,3-dihydroxy2-propoxy)methyl, (2-hydroxyethoxy)methyl, (2-ethoxy)methyl, (2-acetoxyethoxy)methyl, 2-hydroxyl-(1,3-dihydroxy2-propoxy)ethyl, (2-phosphonylmethoxy)ethyl or 3-hydroxy-2-phosphonylmethoxypropyl.

2. The compound of claim 1 wherein $R_1$ is $NH_2$, $R_2$ is Cl, $R_3$ is H and $R_4$ is (2-hydroxyethoxy)methyl.

3. The compound of claim 1 wherein $R_1$ is $NH_2$, $R_2$ is Br, $R_3$ is H and $R_4$ is (2-hydroxyethoxy)methyl.

4. The compound of claim 1 wherein $R_1$ is $NH_2$, $R_2$ is I, $R_3$ is H and $R_4$ is (2-hydroxyethoxy)methyl.

5. The compound of claim 1 wherein $R_1$ is $NH_2$, $R_2$ is thiocarboxamide, $R_3$ is H and $R_4$ is (2-hydroxyethoxy)methyl.

6. The compound of claim 1 wherein $R_1$ is $NH_2$, $R_2$ is Cl, $R_3$ is H and $R_4$ is (1,3-dihydroxy-2-propoxy)methyl.

7. The compound of claim 1 wherein $R_1$ is $NH_2$, $R_2$ is Br, $R_3$ is H and $R_4$ is (1,3-dihydroxy-2-propoxy)methyl.

8. The compound of claim 1 wherein $R_1$ is $NH_2$, $R_2$ is I, $R_3$ is H and $R_4$ is (1,3-dihydroxy-2-propoxy)methyl.

9. The compound of claim 1 wherein $R_1$ is $NH_2$, $R_2$ is thiocarboxamide, $R_3$ is H and $R_4$ is (1,3-dihydroxy-2-propoxy)methyl.

10. The compound of claim 1 wherein $R_1$ is $NH_2$, $R_2$ is thiocarboxamide, $R_3$ is H and $R_4$ is 2-hydroxy-1-(1,3-dihydroxy-2-propoxy)ethyl.

11. The method of treating animal cells infected with a mammalian infectious virus comprising the step of contacting said cells with a composition comprising a compound in an amount sufficient to provide a therapeutic effect on said animal cells, said compound being selected from the group consisting of a compound of the following formula and pharmaceutically acceptable salts thereof:

where
$R_1$ is $NH_2$ or NHOH;
$R_2$ is $CSNH_2$, Cl, Br, I, F, 2-buten1-yl, 5-(1-hydroxyethyl) or 5-(1-methoxyethyl);
$R_3$ is H, $NH_2$ or Br; and
$R_4$ is (1,3-dihydroxy-2-propoxy)methyl, (2-hydroxyethoxy)methyl, (2-ethoxy)methyl, (2-acetoxyethoxy)methyl, 2-hydroxy-1-(1,3-dihydroxy-2-propoxy)ethyl, (2-phosphonylmethoxy)ethyl or 3-hydroxy-2-phosphonylmethoxypropyl.

12. The method of claim 11 wherein the virus is human cytomegalovirus.

13. The method of claim 11 wherein the virus is herpes simplex virus type 1.

14. The method of claim 11 wherein said cells are human cells.

15. The method of claim 11 wherein $R_1$ is $NH_2$, $R_2$ is a halo group, $R_3$ is H and $R_4$ is (1,3-dihydroxy-2-propoxy)methyl.

16. The method of claim 11 wherein $R_1$ is $NH_2$, $R_2$ is a halo group, $R_3$ is H and $R_4$ is (2-hydroxyethoxy)methyl.

17. The method of claim 15 wherein $R_2$ is Cl.

18. The method of claim 15 wherein $R_2$ is Br.

19. The method of claim 16 wherein $R_2$ Cl.

20. The method of claim 16 wherein $R_2$ is Br.

21. The method of claim 16 wherein $R_2$ is I.

22. The method of claim 11 wherein $R_1$ is $NH_2$, $R_2$ is $CSNH_2$, $R_3$ is H and $R_4$ is (1,3-dihydroxy-2-propoxy)methyl.

23. The method of claim 11 wherein $R_1$ is $NH_2$, $R_2$ is $CSNH_2$, $R_3$ is H and $R_4$ is (2-hydroxyethoxy)methyl.

24. The method of claim 11 wherein $R_3$ is $NH_2$.

25. The method of claim 11 wherein $R_3$ is Br.

26. The method of claim 11 wherein said step of contacting occurs in vivo.

* * * * *

UNITED STATES PATENT AND TRADEMARK OFFICE
CERTIFICATE OF CORRECTION

PATENT NO. : 4,927,830

DATED : May 22, 1990

INVENTOR(S) : Leroy B. Townsend and John C. Drach

It is certified that error appears in the above-identified patent and that said Letters Patent is hereby corrected as shown below:

ON THE TITLE PAGE: Other Documents, 1st occurrence of Mitsuya, "3" should be --3'--.

ON THE TITLE PAGE: Other Documents, Maruyama "Purrolo" should be --Pyrrolo--.

Column 1, line 27, "Bergstron" should be --Bergstrom--.

Column 1, line 33, "482-284" should be --482-484--.

Column 2, line 61, "[2,3d]" should be --[2,3-d]--.

UNITED STATES PATENT AND TRADEMARK OFFICE
CERTIFICATE OF CORRECTION

PATENT NO. : 4,927,830

DATED : May 22, 1990

INVENTOR(S) : Leroy B. Townsend and John C. Drach

It is certified that error appears in the above-identified patent and that said Letters Patent is hereby corrected as shown below:

Column 5, last formula of Scheme 2, should be

UNITED STATES PATENT AND TRADEMARK OFFICE
CERTIFICATE OF CORRECTION

PATENT NO. : 4,927,830

DATED : May 22, 1990

INVENTOR(S) : Leroy B. Townsend and John C. Drach

It is certified that error appears in the above-identified patent and that said Letters Patent is hereby corrected as shown below:

Column 8, line 40, "H" 2nd occurrence should be --N--.

Column 8, line 65, "mmol" should be --mmole--.

Column 9, line 28, "C$\underline{H}_2$," should be --C$\underline{H}_2$),--.

Column 12, line 39, "fifty" should be --Fifty--.

Column 12, line 68, "converter" should be --converted--.

Column 14, line 36, "t-test" should be --t-test)--.

Column 15, line 29, "fro" should be --for--.

Column 18, line 57, "UMJD 100)" should be --(UMJD 100)--.

Column 20, line 54, "$R_2$ Cl" should be --$R_2$ is Cl--.

Signed and Sealed this

Thirtieth Day of June, 1992

*Attest:*

DOUGLAS B. COMER

*Attesting Officer*     *Acting Commissioner of Patents and Trademarks*